United States Patent [19]
Derible et al.

[11] 3,975,529
[45] Aug. 17, 1976

[54] DIEBENZO(B,E)THIEPINES

[75] Inventors: Pierre Henri Derible, Le Perreux; Vesperto Torelli, Maisons-Alfort; Claude Dumont, Nogent-sur-Marne, all of France

[73] Assignee: Roussel-UCLAF, Paris, France

[22] Filed: June 24, 1975

[21] Appl. No.: 589,885

[30] Foreign Application Priority Data
July 4, 1974 France .............................. 74.23280

[52] U.S. Cl. ................................ 424/265; 260/292
[51] Int. Cl.² ................ A01N 9/22; C07D 471/08
[58] Field of Search .................... 260/292; 424/265

[56] References Cited
UNITED STATES PATENTS
3,365,457  1/1968  Zenitz ................................ 260/292
3,725,415  4/1973  Boissier et al. .................... 260/292

OTHER PUBLICATIONS
Wagner & Zook, Synthetic Organic Chemistry, Wiley Pub. pp. 92, 171, 481 and 498, (1959).

*Primary Examiner*—Alan L. Rotman
*Attorney, Agent, or Firm*—Hammond & Littell

[57] ABSTRACT

Novel 6,11-dihydrodibenzo(b,e)thiepines of the formula

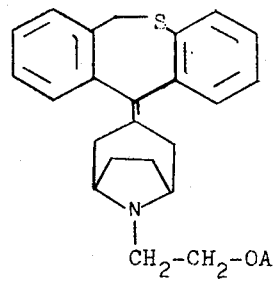

I wherein A is selected from the group consisting of hydrogen and acyl of an alkanoic acid of 2 to 19 carbon atoms in the form of their optically active isomers or racemic mixtures thereof and their non-toxic, pharmaceutically acceptable acid addition salts having remarkable anticholinergic properties.

11 Claims, No Drawings

DIEBENZO(b,e)THIEPINES

STATE OF THE ART

French Pat. No. 1,600,891 describes tropane derivatives which do possess anticholinergic activity but they are structurally different from the compounds of formula I.

OBJECTS OF THE INVENTION

It is an object of the invention to provide the novel dihydrodibenzo(b,e)thiepines of formula I and their non-toxic, pharmaceutically acceptable acid addition salts.

It is another object of the invention to provide a novel process for the preparation of the compounds of formula I.

It is a further object of the invention to provide novel anticholinergic compositions and to provide a novel method of inducing anticholinergic activity in warm-blooded animals.

These and other objects and advantages of the invention will become obvious from the following detailed description.

THE INVENTION

The novel products of the invention are selected from the group consisting of 6,11-dihydrodibenzo(b,e)thiepines of the formula

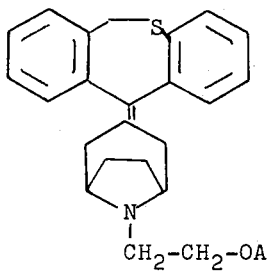

I wherein A is selected from the group consisting of hydrogen and acyl of an alkanoic acid of 2 to 19 carbon atoms in the form of their optically active isomers or racemic mixtures thereof and their non-toxic, pharmaceutically acceptable acid addition salts.

The acyl radical of the organic carboxylic acids for A may have the formula

where R is alkyl of 1 to 18 carbon atoms. Examples of suitable groups for R are methyl, ethyl, propyl, isopropyl, butyl, tert.-butyl, pentyl, isopentyl, neopentyl, hexyl, heptyl, octyl, nonyl, decyl, undecyl, dodecyl, pentadecyl or heptadecyl. Preferably, R is alkyl of 2 to 15 carbon atoms.

Examples of suitable acids for the formation of the non-toxic, pharmaceutically acceptable acid addition salts are inorganic acids such as hydrochloric acid, hydrobromic acid, hydroiodic acid, nitric acid, sulfuric acid or phosphoric acid or organic acids such as acetic acid, formic acid, benzoic acid, maleic acid, fumaric acid, succinic acid, tartaric acid, citric acid, oxalic acid, glyoxylic acid, aspartic acid, alkane sulfonic acids and aryl sulfonic acids.

Among the preferred compounds of the invention are the following compounds or their non-toxic, pharmaceutically acceptable acid addition salts in the form of their optically active isomers or racemic mixtures: N-(β-hydroxyethyl)-11-(3'-nortropylidene)-6,11-dihydrodibenzo(b,e)thiepine; N-(β-propionyloxyethyl)-11-(3'-nortropylidene)-6,11-dihydrodibenzo(b,e)thiepine; N-(β-heptanoyloxyethyl)-11-(3'-nortropylidene)-6,11-dihydrodibenzo(b,e)thiepine; N-(β-decanoyloxyethyl)-11-(3'-nortropylidene)-6,11-dihydrodibenzo(b,e)thiepine; and N-(β-palmitoyloxyethyl)-11-(3'-nortropylidene)6,11-dihydrodibenzo(b,e)thiepine.

The novel process of the invention for the preparation of the 6,11-dihydrodibenzo(b,e)thiepines of formula I comprises reacting a compound of the formula

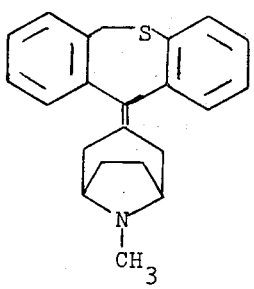

II with an alkyl haloformate of the formula

III wherein X is a halogen and R₁ is alkyl of 1 to 3 carbon atoms to form a compound of the formula

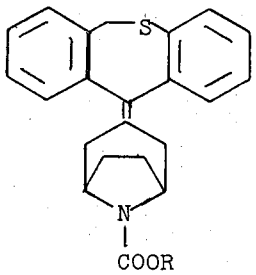

IV subjecting the latter to saponification to form a compound of the formula

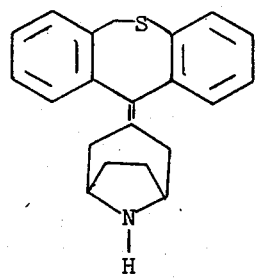

V reacting the latter with 2-[2'-bromoethoxy]-tetrahydropyran of the formula

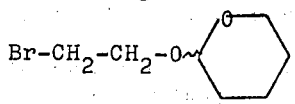

to obtain a compound of the formula

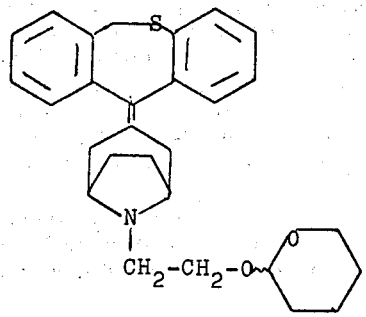

and subjecting the latter to hydrolysis to obtain a compound of formula I wherein A is hydrogen which may be isolated as such or as its acid addition salt or can be reacted with an acid halide of the formula

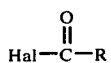

wherein Hal is halogen and R has the above definition to obtain the corresponding ester of formula I which may be isolated as such or as its acid addition salt.

The preferred reaction conditions are as follows: The alkyl haloformate is preferably methyl or ethyl chloroformate and the saponification is effected at reflux with an alkali metal hydroxide such as potassium hydroxide in an organic solvent such as ethylene glycol. The reaction of 2-[2′-bromoethoxy]tetrahydropyran with the compound of formula V is preferably effected in an anhydrous organic solvent such as tetrahydrofuran in the presence of sodium hydride and the hydrolysis of the compound of formula VII is effected in an acid media in an aqueous solution of a low molecular weight alcohol. The acid halide is preferably the acid chloride.

The products of formula I and their acid addition salts exist as racemates or as optically active isomers which can be separated by the usual methods such as resolution of the products by forming salts with an optically active acid.

The novel anticholinergic compositions of the invention are comprised of at least one compound of formula I or its non-toxic, pharmaceutically acceptable acid addition salts and a pharmaceutical carrier. The compositions of the invention may be in the form of tablets, dragees, gelules, granules, suppositories or injectable solutions or suspensions made in the usual manner.

Besides the active principle, the compositions may contain the usual excipients such as talc, arabic gum, lactose, starch, magnesium stearate, cocao butter, aqueous or non-aqueous vehicles, fatty bodies of animal or vegetable origin, paraffinic derivatives, glycols, diverse wetting agents, dispersants or emulsifiers or preservatives.

Depending upon the nature of the A substituent and the method of administration, the properties may be manifested in a more or less prolonged manner. If A is hydrogen, the product may be orally administered and will exhibit the activity for several hours. If A is an acyl radical, the products are preferably administered by injection in an oil solution and the anticholinergic activity is manifested for several weeks.

The compositions of the invention are therefore useful in the treatment of Parkinson disease and in the treatment of extra pyramidal syndromes provoked by administration of neuroleptics.

The novel method of the invention for inducing anticholinergic activity in warm-blooded animals comprises administering to warm-blooded animals an anticholinergic effective amount of at least one compound of formula I or its non-toxic, pharmaceutically acceptable acid addition salts. The compounds may be administered orally, rectally or parenterally. When A is hydrogen and the product is orally administered, the preferred daily dose is 0.04 to 1 mg/kg in human. If A is acyl, the product is preferably administered by intramuscular injection at a rate of 0.2 to 4 mg/kg, each week to each month in human.

The product of formula II used as a starting material may be prepared as described in French Pat. No. 1,600,891. The product of formula V is a noval product useful as an intermediate for the product of formula I.

In the following examples there are described several preferred embodiments to illustrate the invention. However, it should be understood that the invention is not intended to be limited to the specific embodiments.

EXAMPLE 1 dl
N-(β-hydroxyethyl)-11-[3′-nortropylidene]-6,11-dihydrodibenzo(b,e)thiepine hydrochloride STEP A: dl 11-(3′-nortropylidene)-6,11-dihydrodibenzo[b,e]thiepine.

A suspension of 17 g of dl 11-[3′-tropylidene]-6,11-dihydrodibenzo(b,e)thiepine in 53 ml of anhydrous benzene was heated to reflux and 34 ml of ethyl chloroformate were slowly added thereto. The mixture was stirred for 17 hours and dried under reduced pressure. The residue was taken up in 170 ml of ethylene glycol and 17 g of potassium hydroxide pellets were added thereto. The mixture was heated in a metal bath to about 175 to 185°C for 1½ hours and the reaction mixture was then poured into 1000 ml of water. The mixture was vacuum filtered and the solid product was washed with water and dissolved in ether. The ether solution was dried and evaporated to dryness to obtain 16.2 g of raw product which was crystallized from an ether-isopropyl ether mixture to obtain 11.96 g of dl 11-(3′-nortropylidene)-6,11-dihydrodibenzo(b,e)thiepine which was used as is for the next step. For analysis, a sample was crystallized from hot and cold methanol to obtain a product melting at 172°C.

Analysis: $C_{21}H_{21}NS$; molecular weight = 319.472

| | %C | %H | %N | %S |
|---|---|---|---|---|
| Calculated: | 78.95 | 6.62 | 4.38 | 10.04 |
| Found: | 79.1 | 6.7 | 4.2 | 9.9 |

STEP B: dl N-[β-(RS)-tetrahydropyranyloxyethyl]-11-(3′-nortropylidene)-6,11-dihydrodibenzo(b,e)thiepine A mixture of 30 ml of anhydrous tetrahydrofuran, 3 g of a dispersion of 50% sodium hydroxide in oil and 8.88 g of dl 11-(3′-nortropylidene)-6,11-dihydrodibenzo(b,e)thiepine was heated to reflux under a nitrogen atmosphere and after 10 minutes, 9 ml of 2 RS-(2′-bromoethoxy)-tetrahydropyran [J. Chem. Soc., Vol.

70 (1948), p. 4187] were added dropwise. Reflux was maintained for 15 hours and was then iced. A solution of 10% tetrahydrofuran in water was slowly added thereto and the mixture was diluted with water and extracted with methylene chloride. The organic extracts were washed with water, dried and distilled to dryness to obtain 19 g of a yellow oil. The oil was purified by chromatography over silica gel and elution with a 1—1 mixture of hexane (b.p. 70°C) and diethyl ether containing 2% of triethylamine to obtain 4 fractions. After inducing crystallization of the different fractions in ether solution, 9.93 g of dl N-[β-RS-tetrahydropyranyloxyethyl]-11-(3′-nortropylidene)-6,11-dihydrodibenzo(b,e)thiepine were obtained which had a homogenous thin layer chromatography and same Rf and melted at 125° and 142°C.

STEP C: dl N-(β-hydroxyethyl)-11-(3′-nortropylidene)-6,11-dihydrodibenzo(b,e)thiepine.

8.4 ml of water were added to a suspension of 8.41 g of dl N-[β-(RS)-tetrahydropyranyloxyethyl]-11-(3′-nortropylidene)-6,11-dihydrodibenzo(b,e)thiepine in 84 ml of methanol and then 8.4 ml of hydrochloric acid were added thereto. The solution stood at room temperature for 2½ hours and then was cooled and made alkaline by addition of 2N sodium hydroxide solution. The precipitate formed was extracted with methylene chloride and the extracts were washed with water, dried and distilled to dryness to obtain 8.4 g of raw product. The product was crystallized from ether and dried to obtain 6.48 g of dl N-(β-hydroxyethyl)-11-(3′-nortropylidene)6,11-dihydrodibenzo(b,e)thiepine.

10.2 g of the said product obtained from two successive preparations were dissolved in 50 ml of refluxing ethyl acetate and the solution was filtered while hot. The filter was rinsed with ethyl acetate and the filtrate was concentrated. Crystallization was induced and after being iced for an hour, the mixture was vacuum filtered. The solid product was washed with a minimum of iced ethyl acetate and dried at 80°C under reduced pressure to obtain 7.5 g of dl N-(β-hydroxyethyl)-11-(3′-nortropylidene)-6,11-dihydrodibenzo(b,e)thiepine in the form of a colorless solid melting at 164°C.

Analysis: $C_{23}H_{25}NOS$

| | %C 76.00 | %H 6.93 | %N 3.85 | %S 8.82 |
|---|---|---|---|---|
| Calculated: | 76.00 | 6.93 | 3.85 | 8.82 |
| Found: | 75.9 | 7.1 | 3.6 | 8.7 |

STEP D: dl N-(β-hydroxyethyl)-11-(3′-nortropylidene)-6,11-dihydrodibenzo(b,e)thiepine hydrochloride 20 ml of isopropanol, 30 ml of methanol, 2 ml of concentrated hydrochloric acid and 25 ml of water were added to 6.5 g of dl N-(β-hydroxyethyl)-11-(3′-nortropylidene)-6,11-dihydrodibenzo(b,e)thiepine and the solution was decolorized by filtration after contact with 50 mg of activated charcoal. The filtrate was evaporated at a temperature less than 30°C and the residue was taken up in 50 ml of isopropanol which was then evaporated under reduced pressure. The crystalline residue was empasted with isopropanol and then was vacuum filtered. The solid was washed with isopropanol and then ether and dried to obtain 6.92 g of dl N-(β-hydroxyethyl)-11-(3′-nortropylidene)-6,11-dihydrodibenzo(b,e)thiepine hydrochloride as a colorless solid melting at 258°–261°C.

Analysis: $C_{23}H_{26}ClNOS$; molecular weight = 399.98

| | %C 69.06 | %H 6.55 | %Cl 8.863 | %N 3.50 | %S 8.02 |
|---|---|---|---|---|---|
| Calculated: | 69.06 | 6.55 | 8.863 | 3.50 | 8.02 |
| Found: | 68.9 | 6.5 | 8.8 | 3.3 | 8.0 |

EXAMPLE 2 dl N-(β-propionyloxyethyl)-11-(3′-nortropylidene)-6,11-dihydrodibenzo(b,e)thiepine STEP A: dl N-(β-propionyloxyethyl)-11-(3′-nortropylidene)-6,11-dihydrodibenzo(b,e)thiepine hydrochloride 18 ml of propionyl chloride were added to a suspension of 6 g of dl N-(β-hydroxyethyl)-11-(3′-nortropylidene)-6,11-dihydrodibenzo(b,e)thiepine hydrochloride in 60 ml of anhydrous tetrahydrofuran and the mixture was refluxed for 2 hours and was then concentrated under a slight vacuum. The mixture was distilled to about 45 ml and was then iced and vacuum filtered. The crystals were washed with ether and dried to obtain a raw product which was dissolved in methylene chloride. The solution was filtered and the filtrate was diluted with tetrahydrofuran. Th solution was concentrated, iced and vacuum filtered and the solid product was washed with ether to obtain 5.89 g of dl N-(β-propionyloxyethyl)-11-(3′-nortropylidene)-6,11-dihydrodibenzo(b,e)thiepine hydrochloride as a colorless solid melting at about 210°C.

Analysis: $C_{26}H_{30}ClNO_2S$

| | %C 68.47 | %H 6.63 | %Cl 7.77 | %N 3.07 | %S 7.03 |
|---|---|---|---|---|---|
| Calculated: | 68.47 | 6.63 | 7.77 | 3.07 | 7.03 |
| Found: | 68.2 | 6.7 | 7.7 | 3.0 | 7.0 |

STEP B: dl N-(β-propionyloxyethyl)-11-(3′-nortropylidene)-6,11-dihydrodibenzo(b,e)thiepine.

Sodium bicarbonate was added to a solution of 5.79 g of the product of Step A in 100 ml of water and 120 ml of methanol until the pH was alkaline and the mixture was extracted with methylene chloride. The extract was washed with water, dried and distilled to dryness to obtain 5.3 g of raw product. The product was purified by chromatography over silica gel and elution with a 97.5–2.5 chloroform-methanol mixture to obtain 5.08 g of dl N-(β-propionyloxyethyl)-11-(3′-nortropylidene)-6,11-dihydrodibenzo(b,e)thiepine was a pale yellow oil.

EXAMPLE 3 dl N-(β-heptanoyloxyethyl)-11-(3′-nortropylidene)-6,11-dihydrodibenzo(b,e)thiepine Using the procedure of Step A of Example 2, a solution of 2.875 g of dl N-(β-hydroxyethyl)-11-(3′-nortropylidene)-6,11-dihydrodibenzo(b,e)thiepine in 28.7 ml of anhydrous tetrahydrofuran and 6 ml of heptanoyl chloride were reacted to obtain 2.52 g of dl N-(β-heptanoyloxyethyl)-11-(3′-nortropylidene)-6,11-dihydrodibenzo(b,e)thiepine hydrochloride as a colorless solid melting at 160°C.

Analysis: $C_{30}H_{38}ClNO_2S$

Calculated: %C 70.35  %H 7.47  %Cl 6.92  %N 2.73 %S 6.26
Found:           70.3       7.6        7.0           2.6   6.2

Using the procedure of Step B of Example 2, 2.46 g of dl N-(β-heptanoyloxyethyl)-11-(3'-nortropylidene)-6,11-dihydrodibenzo(b,e)thiepine hydrochloride in 100 ml of water and 60 ml of ethanol resulted in 2.29 g of dl N-(β-heptanoyloxyethyl)-11-(3'-nortropylidene)-6,11-dihydrodibenzo(b,e)thiepine as a pale yellow oil.

EXAMPLE 4 dl N-(β-decanoyloxyethyl)-11-(3'-nortropylidene)-6,11-dihydrodibenzo(b,e)thiepine 18 ml of decanoyl chloride were added to a mixture of 6.37 g of dl N-(β-hydroxyethyl)-11-(3'-nortropylidene)-6,11-dihydrodibenzo(b,e)thiepine hydrochloride in 64 ml of tetrahydrofuran and the suspension was refluxed for 3½ hours and then concentrated under reduced pressure. The pale yellow oil residue was taken up in 300 ml of isopropyl ether and after stirring the isopropyl ether was decanted. The insoluble fraction was dissolved in 100 ml of ethanol and then 50 ml of water and a saturated sodium bicarbonate solution were added thereto. The mixture was extracted with methylene chloride and the organic extracts were washed with water, dried and evaporated to dryness under reduced pressure to obtain 8.45 g of raw product. The product was chromatographed over silica gel and was eluted with a 97.5-2.5 chloroform-methanol mixture which after evaporation gave 6.55 g of dl N-(β-decanoyloxyethyl)-11-(3'-nortropylidene)-6,11-dihydrodibenzo(b,e)thiepine as a pale yellow oil.

| UV Spectra (ethanol): | |
|---|---|
| Max. — 229.5 nm | $\epsilon = 22,000$ |
| Inflex. — 259 nm | $\epsilon = 9,250$ |
| Max. — 300 nm | $\epsilon = 2,200$ |

EXAMPLE 5 dl N-(β-palmitoyloxyethyl)-11-(3'-nortropylidene)-6,11-dihydrodibenzo(b,e)thiepine 15 ml of palmitoyl chloride were added to 5 g of dl N-(β-hydroxyethyl)-11-(3'-nortropylidene)-6,11-dihydrodibenzo(b,e)thiepine hydrochloride in 50 ml of tetrahydrofuran and the mixture was refluxed for 8½ hours and concentrated to dryness under reduced pressure. The oil residue was diluted with iced water and the aqueous phase was made alkaline with triethylamine. The mixture was extracted with methylene chloride and the organic phase was acidified with acetic acid and was filtered. The filtrate was washed with water, dried and evaporated to dryness under reduced pressure to obtain 13 g of a mixture of palmitic acid and a palmitate. The mixture was chromatographed over silica gel and the palmitic acid was first eluted with a 1—1 benzene-ethylacetate mixture containing 2% of acetic acid. The column was then eluted with a 1—1 benzene-ethylacetate mixture containing 2% of triethylamine and the eluate was evaporated. The oil residue was taken up in methylene chloride and the solution was washed with water and dried to obtain 5.9 g of dl N-(β-palmitoyloxyethyl)-11-(3'-nortropylidene)-6,11-dihydrodibenzo(b,e)thiepine as a pale yellow oil.

| UV Spectra (ethanol): | |
|---|---|
| Max. — 228 nm | $\epsilon = 22,800$ |
| Inflex. — 260 nm | |
| Max. — 300 – 301 nm | $\epsilon = 2,200$ |

EXAMPLE 6

Tablets were prepared which contained 5 mg of dl N-(β-hydroxyethyl)-11-(3'-nortropylidene)-6,11-dihydrodibenzo(b,e)thiepine hydrochloride and sufficient excipient consisting of starch, lactose, talc and magnesium stearate to obtain a tablet of 200 mg.

Injectable solutions were prepared to obtain 25 mg of dl N-(β-propionyloxyethyl)-11-(3'-nortropylidene)-6,11-dihydrodibenzo(b,e)thiepine or dl N-(β-decanoyloxyethyl)-11-(3'-nortropylidene)-6,11-dihydrodibenzo(b,e)thiepine in 1 ml of sesame oil.

PHARMACOLOGICAL DATA

The anticholinergic activity of the products of the invention was demonstrated by their activity against tremorine and oxotremorine which has been used to produce experimental parkinsonism.

A. Antitremorine Activity

The antagonism of the test compounds to the trembling and peripherical cholinergic manifestations provoked by tremorine [Everett et al, Science, Vol. 124 (1956), p. 79] was studied on mice.

The product of Example 1 in aqueous solution was intraperitoneally administered at doses of 0.5, 1,2 and 5 mg/kg to groups of 10 mice and the mice received an intraperitoneal injection of 20 mg/kg of tremorine half an hour after the test product. The reactions (trembling, salivation, lacrymation) of the animals were observed 10, 20, 30 and 60 minutes after the tremorine injection. At the height of the activity, the 50% efficacy dose ($ED_{50}$) in which 50% of the animals were protected from the trembling and peripheral parasympathomimetic reactions of salivation and lacrymation normally provoked by tremorine injection were determined. The $ED_{50}$ dose for the product of Example 1 was 1 mg/kg for trembling and between 1 and 2 mg/kg for parasympathomimetic reactions which showed that the product had an important anticholinergic activity.

The products of Examples 2 and 3 were administered subcutaneously in sesame oil solution at doses of 200 and 400 mg/kg at a volume of 25 ml/kg to groups of 10 mice. The mice receied intraperitoneal injections of 20 mg/kg of tremorine either for 4 hours, one day, 2, 3 or 4 days after injection of the test product. Controls did not receive any sesame oil. The reactions (T-trembling; S-salivation; L-lacrymation) were noted 10, 20, 30 and 60 minutes after the tremorine injection and the percent of inhibition of the different reactions at the height of the effect after injection of tremorine were noted as a function of time. The results are in Table I.

TABLE I

| Products of Example | Doses in mg/Kg | Reactions | % inhibition of reactions after | | | | |
|---|---|---|---|---|---|---|---|
| | | | 4 h | 1 d | 2 d | 3 d | 4 d |
| 2 | 200 | T | 100 | 90 | 0 | 20 | 0 |
| | | S | 90 | 90 | 0 | 50 | 0 |
| | | L | 100 | 100 | 40 | 100 | 60 |
| | 400 | T | 100 | 100 | 40 | 10 | 50 |
| | | S | 100 | 100 | 70 | 20 | 90 |
| | | L | 100 | 100 | 100 | 100 | 60 |
| 3 | 200 | T | 40 | 0 | 100 | | 20 |
| | | S | 30 | 20 | 10 | 0 | 10 |
| | | L | 90 | 30 | 100 | 20 | 0 |

The results of Table I show that the products of Examples 2 and 3 possess a prolonged antitremorine activity in the time.

B. Antioxotremorine Activity

1. Antagonism to the trembling and peripherial cholinergic manifestations.

The antagonism of the test products to the trembling and peripherial cholinergic manifestations provoked by oxotremorine [Cho et al, J. Biochem. Biophys. Res. Commun., Vol. 5, (1961) p. 276] was studied on mice. The product of Example 1 was administered subcutaneously in aqueous solution at doses of 50 and 100 mg/kg to groups of 10 mice and the products of Example 2 were subcutaneously administered in sesame oil solution at doses of 200 and 400 mg/kg to groups of 10 mice. Control animals received no vehicle. The mice then received a single intraperitoneal dose of 0.5 mg/kg of oxotremorine either 4 hours, 1 day, 2, 3, 4 or 7 days after the injection of the test product. The reaction of the animals as in Table I were recorded 5,10 and 15 minutes after the injection of oxotremorine and the percent of inhibition of the different reactions, at the height of the effect, after the oxotremorine injection was determined as a function of time. The results are reported in Table II.

TABLE II

| Products of Example | Doses in mg/Kg | Reactions | % inhibition of reactions after | | | | | |
|---|---|---|---|---|---|---|---|---|
| | | | 4 h | 1 d | 2 d | 3 d | 4 d | 7 d |
| 1 | 50 | T | 100 | 0 | | | | |
| | | S | 100 | 0 | | | | |
| | | L | 100 | 0 | | | | |
| | 100 | T | 100 | 0 | | | | |
| | | S | 100 | 0 | | | | |
| | | L | 100 | 0 | | | | |
| 2 | 200 | T | 80 | 100 | 30 | 0 | | 0 |
| | | S | 80 | 90 | 30 | 10 | 0 | 0 |
| | | L | 100 | 100 | 70 | 30 | 11 | 10 |
| | 400 | T | 100 | 100 | 70 | 0 | 20 | 10 |
| | | S | 100 | 100 | 60 | 20 | 20 | 20 |
| | | L | 100 | 100 | 80 | 10 | 67 | 20 |

The results of Table II show that the product of Example 2 has a prolonged antioxotremorine activity.

2. Antagonism of antinociceptive activity of oxotremorine.

The antinociceptive activity of oxotremorine [Leslie, J. Pharm. Pharmae., Vol. 2 (1969), p. 248–50] was determined on mice using the hot plate method of Eddy et al [J. Pharmacol. Vol. 107 (1953), p. 385] in the presence and absence of the test product presumed to be antagonistic. The product of Example 1 was administered subcutaneously in aqueous solution at doses of 50 and 100 mg/kg to groups of 10 mice and the products of Examples 2 to 5 were subcutaneously administered in sesame oil solution at doses of 200 and 400 mg/kg to groups of 10 mice. The mice then received a single intraperitoneal injection of 0.5 mg/kg of oxotremorine either 4 hours, 1 day, 2, 3, 4 or 7 days after the test product administration. For each time considered, the mice were placed on the hot plate one half hour after the oxotremorine administration and the time for the appearance of nociceptive refluxes consistuted by simultaneous licking of the front paws was noted. The maximum time of staying on the hot plate was fixed at 45 seconds and the percentage of animals with a reaction time (RT) less than 40 seconds in spite of oxotremorine administration was determined. The results are reported in Table III.

TABLE III

| Product of Example | Doses in mg/Kg | % of animals with a RT less than 40 seconds after | | | | | |
|---|---|---|---|---|---|---|---|
| | | 4 h | 1 d | 2 d | 3 d | 4 d | 7 d |
| Absolute controls | — | 100 | 100 | 100 | 100 | 100 | 100 |
| Oxotremorine Controls | — | 10 | 10 | 10 | 10 | 0 | 0 |
| 1 | 50 | 100 | 10 | | | | |
| | 100 | 100 | 20 | | | | |
| 2 | 200 | 100 | 100 | 90 | 50 | 60 | 30 |
| | 400 | 100 | 100 | 100 | 80 | 90 | 20 |
| 3 | 200 | 50 | 60 | 50 | 50 | 40 | 40 |
| | 400 | 70 | 40 | 50 | 30 | 40 | 20 |
| 4 | 200 | 100 | 30 | 30 | 10 | 0 | 20 |
| | 400 | 100 | 60 | 30 | 30 | 0 | 30 |
| 5 | 200 | 20 | 30 | 40 | 10 | 30 | 30 |
| | 400 | 70 | 60 | 30 | 20 | 20 | 30 |

The results of Table III show that the product of Example 1 has an important antagonistic activity against antinociceptive activity of oxotremorine which is manifested for several hours while the products of Examples 2 to 5 show the said activity for several days to varying degrees.

C. Acute toxicity study

The acute toxicity of the products was determined intraperitoneally or subcutaneously on mice weighing about 20 g with the $LD_{50}$ dose being calculated by the method of Litchfield et al [J. Pharmacol. exp. Therap., Vol. 96 (1949), p. 99–133]. The $LD_{50}$ for the product of Example 1 in aqueous solution was about 100 mg/kg intraperitoneally after 2 days of observation and about 500 mg/kg subcutaneously after 5 days of observation. The $LD_{50}$ for the products of Examples 2 to 5 in sesame oil solution administered subcutaneously was greater than 400 mg/kg after 7 days of observation.

Various modifications of the products and methods of the invention may be made without departing from the spirit or scope thereof and it should be understood that the invention is intended to be limited only as defined in the appended claims.

We claim:

1. A compound selected from the group consisting of 6,11-dihydrodibenzo(b,e)thiepines of the formula

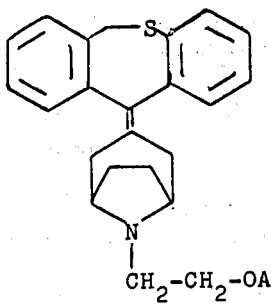

wherein A is selected from the group consisting of hydrogen and acyl of an alkanoic acid of 2 to 19 carbon atoms in the form of their optically active isomers or racemic mixtures thereof and their non-toxic, pharmaceutically acceptable acid addition salts.

2. A compound of claim 1 wherein A is an acyl of 3 to 16 carbon atoms.

3. A compound of claim 1 selected from the group consisting of N-(β-hydroxyethyl)-11-(3'-nortropylidene)-6,11-dihydrodibenzo(b,e)thiepine and its non-toxic, pharmaceutically acceptable acid addition salts.

4. A compound of claim 1 selected from the group consisting of N-(β-propionyloxyetyl)-11-(3'-nortropylidene)-6,11-dihydrodibenzo(b,e)thiepine and its non-toxic, pharmaceutically acceptable acid addition salts.

5. A compound of claim 1 selected from the group consisting of N-(β-heptanoyloxyethyl)-11-(3'-nortropylidene)-6,11-dihydrodibenzo(b,e)thiepine and its non-toxic, pharmaceutically acceptable acid addition salts.

6. A compound of claim 1 selected from the group consisting of N-(β-decanoyloxyethyl)-11-(3'-nortropylidene)-6,11-dihydrodibenzo(b,e)thiepine and its non-toxic, pharmaceutically acceptable acid addition salts.

7. A compound of claim 1 selected from the group consisting of N-(β-palmitoyloxyethyl)-11-(3'-nortropylidene)-6,11-dihydrodibenzo(b,e)thiepine and its non-toxic, pharmaceutically acceptable acid addition salts.

8. An anticholinergic composition comprising an effective amount of a compound of claim 1 and an inert pharmaceutical carrier.

9. A composition of claim 1 wherein A is selected from the group consisting of hydrogen or acyl of propionic acid, heptanoic acid, palmitic acid or decanoic acid.

10. A method of inducing anticholinergic activity in warm-blooded animals comprising administering to warm-blooded animals an anticholinergic effective amount of a compound of claim 1.

11. The method of claim 10 wherein A is selected from the group consisting of hydrogen or acyl of propionic acid, heptanoic acid, palmitic acid or decanoic acid.

* * * * *